United States Patent [19]
Badoz

[11] Patent Number: 5,944,523
[45] Date of Patent: Aug. 31, 1999

[54] DENTAL ASSEMBLY HAVING MULTI-MOVEMENT MOTOR

[75] Inventor: Jean-Marie Badoz, Doubs, France

[73] Assignee: Micro-Mega International Manufactures, Besancon, France

[21] Appl. No.: 08/874,014

[22] Filed: Jun. 12, 1997

[30] Foreign Application Priority Data

Jun. 12, 1996 [FR] France .................................. 96 07467

[51] Int. Cl.⁶ ..................................................... A61C 1/12
[52] U.S. Cl. ............................................. 433/131; 433/114
[58] Field of Search .................................. 433/114, 118, 433/119, 122, 123, 131, 132, 133

[56] References Cited

U.S. PATENT DOCUMENTS

| | | | |
|---|---|---|---|
| 4,505,676 | 3/1985 | Gonser | 433/119 |
| 4,744,752 | 5/1988 | Nakayama et al. | 433/132 X |
| 4,983,901 | 1/1991 | Lehmer | 604/65 X |
| 5,145,369 | 9/1992 | Lustig et al. | 433/118 |
| 5,453,008 | 9/1995 | Berlin | 433/118 X |
| 5,529,494 | 6/1996 | Vlacancich | 433/118 X |
| 5,538,423 | 7/1996 | Coss et al. | 433/131 X |
| 5,720,742 | 2/1998 | Zacharias | 606/1 |

*Primary Examiner*—Nicholas D. Lucchesi
*Attorney, Agent, or Firm*—Weiser & Associates, P.C.

[57] ABSTRACT

A motor and handpiece assembly for driving a dental tool has a contra-angle and a motor. The contra-angle has a handle, a neck connected to the handle, and a head connected to the neck and adapted to hold the dental tool. The motor is adapted to drive the dental tool in different types of movement (e.g., continuous movement and alternating or vibratory movement). The invention provides a dental handpiece that can be used for different types of treatments using different types of dental tools that require different types of movement and different speeds.

8 Claims, 1 Drawing Sheet

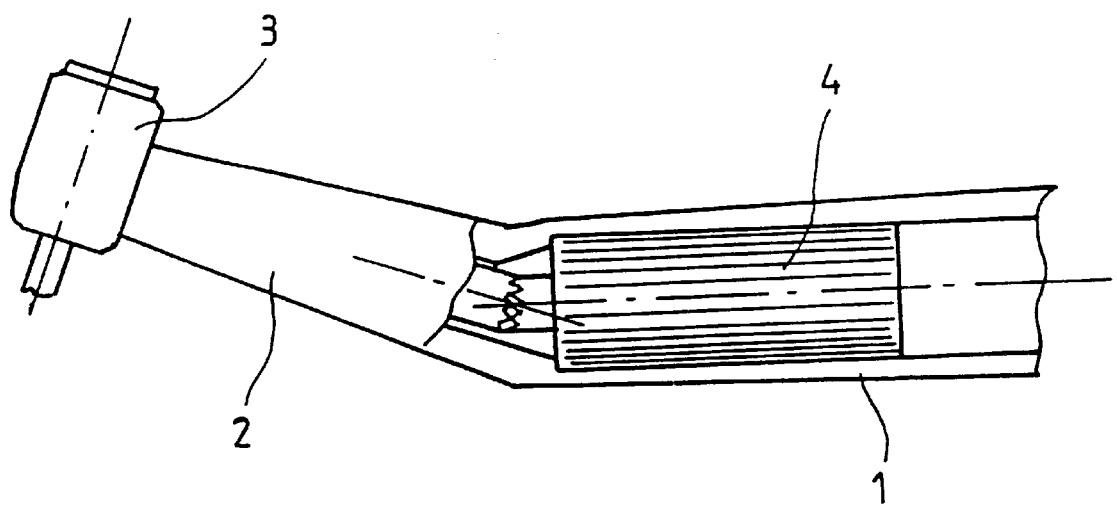

DENTAL ASSEMBLY HAVING MULTI-MOVEMENT MOTOR

BACKGROUND OF THE INVENTION

1. Field of the Invention

The present invention relates to the field of the handpieces used in dentistry, and, more particularly, to the field of handpieces having an integrated drive motor.

2. Description of the Related Art

Dental practice traditionally requires the use of instruments with different speeds of rotation and with different types of movements (continuous rotation, alternating rotary movement, etc.). To reduce the cleaning, disinfecting, and sterilizing work required in the fight against the risks of cross-contamination, it is advantageous to provide the dentist with a tool that can be used for a wide range of treatments. Among the methods of endodontic treatment, some require a continuous movement, while others require an alternating or vibratory movement.

Contra-angles with integrated motors do exist, but these permit only one type of movement, and this is done either with an air motor or an electric motor. None of these solutions of the prior art enables the dentist to choose the speed on the one hand and the type of movement on the other hand.

One object of the invention, among others, is to overcome these disadvantages. Further aspects and advantages of this invention will become apparent from the detailed description which follows.

SUMMARY OF THE INVENTION

The invention is directed to a novel motor and handpiece assembly, more particularly with contra-angle, for driving root canal instruments or other dental instruments, comprising a contra-angle handle, a contra-angle neck, and a contra-angle head, wherein the motor is of the stepping motor variety and is able to drive a dental tool at two or more types of movement. This stepping motor can be placed either in the contra-angle handle, neck, or head.

BRIEF DESCRIPTION OF THE DRAWINGS

Other aspects, features, and advantages of the present invention will become more fully apparent from the following detailed description, the appended claims, and the accompanying drawings in which the single FIGURE is a longitudinal view of a motor and handpiece assembly according to the invention.

DETAILED DESCRIPTION

The motor and handpiece assembly comprises a contra-angle, having a contra-angle handle (1), a contra-angle neck (2), and a contra-angle head (3). The motor (4) is placed in the contra-angle handle (1), as illustrated in the FIGURE. Alternatively, the motor (4) can be placed in the contra-angle neck (2) or in the contra-angle head (3).

The motor (4) is controlled by a control device (5) situated in a housing or control assembly to which the contra-angle is connected via a lead (6). This lead integrates various additional equipment known in dentistry (e.g., air spray, water spray, cooling water). The housing for the control device may be integrated in the dental unit.

The use, in the motor and handpiece assembly, and more particularly with contra-angle, of a motor of the stepping motor variety allows the dentist to benefit from all of the advantages of this type of motor, namely (a) rotation to the right or the left, (b) speed control (continuous operating speed), (c) precise speed regulation, and (d) programming of combined movement (rotation to the right and the left, etc.). By effecting right and left rotations of low angular amplitude, it is possible to generate a vibration in a cannular instrument, which makes it possible to perform endodontic applications as with an air-driven handpiece.

It will be further understood that various changes in the details, materials, and arrangements of the parts which have been described and illustrated in order to explain the nature of this invention may be made by those skilled in the art without departing from the principle and scope of the invention as expressed in the following claims.

What is claimed is:

1. A motor and handpiece assembly for driving a dental tool, comprising:

a contra-angle having a handle, a neck connected to the handle, and a head connected to the neck and adapted to hold the dental tool; and a stepping motor adapted to drive the dental tool in two or more different types of movement.

2. The motor and handpiece assembly as claimed in claim 1, wherein the motor is placed in the handle.

3. The motor and handpiece assembly as claimed in claim 1, wherein the motor is controlled by a control device to which the assembly is connected via a lead.

4. The motor and handpiece assembly as claimed in claim 3, wherein the lead is adapted to integrate at least one of air spray, water spray, and cooling water.

5. The motor and handpiece assembly as claimed in claim 3, wherein the motor is placed in the handle.

6. The motor and handpiece assembly as claimed in claim 3, wherein the control device is integrated in the assembly.

7. The motor and handpiece assembly as claimed in claim 1, wherein the different types of movement include continuous movement and alternating movement.

8. The motor and handpiece assembly as claimed in claim 1, wherein the motor is adapted to drive the dental tool in right and left rotations.

* * * * *